United States Patent [19]
Habuchi

[11] Patent Number: 5,955,325
[45] Date of Patent: Sep. 21, 1999

[54] METHOD FOR PRODUCING SULFATED LACTOSAMINE OLIGOSACCHARIDE

[75] Inventor: Osami Habuchi, Nagoya, Japan

[73] Assignee: Seikagaku Kogyo Kabushiki Kaisha, Tokyo, Japan

[21] Appl. No.: 08/829,368

[22] Filed: Mar. 31, 1997

[30] Foreign Application Priority Data

Mar. 29, 1996 [JP] Japan ..................... 8-077784

[51] Int. Cl.$^6$ ............. C12P 19/12; C12P 19/04; C12P 11/00
[52] U.S. Cl. ............. 435/100; 435/101; 435/130; 435/74; 435/72
[58] Field of Search ................. 435/100, 101, 435/130, 74, 72

[56] References Cited

U.S. PATENT DOCUMENTS

| | | | |
|---|---|---|---|
| 5,288,637 | 2/1994 | Roth | 435/288 |
| 5,374,541 | 12/1994 | Wong et al. | 435/74 |
| 5,580,862 | 12/1996 | Rosen et al. | 514/61 |

OTHER PUBLICATIONS

Habuchi et al, J. Biol. Chem. 268(29):21968–21974 (1993).

*Primary Examiner*—Francisco Prats
*Attorney, Agent, or Firm*—Knobbe, Martens, Olson & Bear, LLP

[57] ABSTRACT

Disclosed is a method for producing a sulfated lactosamine oligosaccharide, comprising the step of allowing a sulfotransferase to act on a lactosamine oligosaccharide, the sulfotransferase transferring sulfate group to hydroxyl group at C-6 position of galactose residue in the lactosamine oligosaccharide.

13 Claims, 10 Drawing Sheets

METHOD FOR PRODUCING SULFATED LACTOSAMINE OLIGOSACCHARIDE

BACKGROUND OF THE INVENTION

The present invention relates to a novel method for producing a sulfated lactosamine oligosaccharide. In particular, the present invention relates to a method for producing a sulfated lactosamine oligosaccharide from a lactosamine oligosaccharide based on the use of an enzyme reaction.

Sugar chains composed of lactosamine backbones serve as the ligand sugar chain which has the ability to bind cell adhesion molecules belonging to the selectin family, and thus they express important physiological activities in vivo. It has been clarified that expression of such sugar chains on cell surfaces participates in specific adhesion between heterogeneous cells. Functional activating agents and suppressing agents based on the utilization of these sugar chains are expected to be useful drugs. Namely, it is believed that these sugar chains include their principal compound of sialyl Lewis$^x$ (SLe$^x$) and its analogs with which the selectin molecule is blocked to inhibit adhesion between lymphocyte and endothelial cell, and thus they are useful to mitigate various diseases associated with inflammation. In addition, it is also believed that these sugar chains participate in adhesion to endothelial cells upon hematogenous metastasis of tumor cells, and they participate in adhesion to target cells upon infection with microorganisms. Therefore, these sugar chains are regarded to be important as materials to develop pharmaceuticals for preventing such diseases.

On the other hand, one of the ligands for L-selectin (expressed on lymphocyte) which participates in homing of lymphocyte and rolling of leukocyte caused at an initial stage of inflammation is considered to be "GlyCAM-1 (highly glycosylated cell adhesion molecule-1, glycosylation-dependent cell adhesion molecule-1; expressed on blood vessel endothelium)", and the sugar chain occupies not less than 70% of GlyCAM-1. Recently, GlyCAM-1 attracts great attention together with a basic backbone of the sugar chain (NeuAc-Gal(6S)—(Fuc-)GlcNAc—R, wherein NeuAc represents an N-acetylneuraminic acid residue, Gal represents a galactose residue, (6S) indicates that hydroxyl group at C-6 position is sulfated, Fuc represents a fucose residue, GlcNAc represents an N-acetylglucosamine residue,—represents a glycoside linkage, and R represents a hydrogen atom or a sugar chain: this basic backbone is hereinafter referred to as "basic backbone of GlyCAM-1 sugar chain", if necessary).

GlyCAM-1 and the basic backbone of its sugar chain are expected to play important roles in development of novel pharmaceuticals and in studies on physiological activities in vivo. It is desired to stably supply these substances. However, at present, they can be obtained only from animals which express GlyCAM-1. Therefore, obtainable amounts are minute. It is difficult to produce GlyCAM-1 and the basic backbone of its sugar chain by means of organic synthesis. However, no method has been known for producing a sulfated lactosamine oligosaccharide which can be converted into the basic backbone of the GlyCAM-1 sugar chain.

The present invention has been made taking the aforementioned viewpoints into consideration, an object of which is to provide a novel method for producing a sulfated lactosamine oligosaccharide in order to obtain the basic backbone of the GlyCAM-1 sugar chain.

SUMMARY OF THE INVENTION

As a result of diligent studies by the present inventors in order to achieve the object described above, it has been found that a sulfated lactosamine oligosaccharide can be obtained by allowing a sulfotransferase to act on a lactosamine oligosaccharide, the sulfotransferase transferring sulfate group to hydroxyl group at C-6 position of galactose residue in the lactosamine oligosaccharide. Thus the present invention has been completed.

Namely, the present invention provides a method for producing a sulfated lactosamine oligosaccharide, comprising the step of allowing a sulfotransferase to act on a lactosamine oligosaccharide, the sulfotransferase transferring sulfate group to hydroxyl group at C-6 position of galactose residue in the lactosamine oligosaccharide.

The term "lactosamine" herein include lactosamine (a substance in which a galactose residue is bound to a glucosamine residue through a glycoside linkage; represented by Gal—GlcN), as well as N-acetyllactosamine (a substance in which a galactose residue is bound to an N-acetylglucosamine residue through a glycoside linkage; represented by Gal—GlcNAc). In the formulas described herein, Gal represents a galactose residue, GlcNAc represents an N-acetylglucosamine residue, GlcN represents a glucosamine residue, SA represents a sialic acid residue, NeuAc represents an N-acetylneuraminic acid residue, Fuc represents a fucose residue, (6S) indicates that hydroxyl group at hydroxyl group at C-6 position is sulfated, and— represents a glycoside linkage.

The term "lactosamine" herein includes lactosamine containing a sialic acid residue and/or a fucose residue. The term "lactosamine oligosaccharide" herein refers to an oligosaccharide containing at least one lactosamine, which includes, for example, lactosamine itself, oligosaccharides containing at least one lactosamine, and oligosaccharides comprising a basic backbone of a repeating structure composed of lactosamines. The term "lactosamine oligosaccharide" includes those containing a sulfated glucosamine residue (or a sulfated N-acetylglucosamine residue) and/or a sulfated galactose residue provided that they are lactosamine oligosaccharides containing at least one lactosamine having a galactose residue which is not sulfated at its hydroxyl group at C-6 position. The term "sulfated lactosamine oligosaccharide" herein means a substance in which sulfate group is added to a part or all of hydroxyl groups at C-6 positions of nonsulfated galactose residues in the lactosamine oligosaccharide. The description of only "lactosamine" herein means lactosamine itself, as well as a lactosamine structure (backbone) in the lactosamine oligosaccharide.

According to the present invention, a sulfated lactosamine oligosaccharide can be produced from a lactosamine oligosaccharide. The sulfated lactosamine oligosaccharide obtained by the method of the present invention is expected to be utilized as an intermediate to obtain the basic backbone of GlyCAM-1 sugar chain. GlyCAM-1 and the basic backbone of GlyCAM-1 sugar chain can be utilized as anti-inflammatory agents.

DETAILED DESCRIPTION OF THE INVENTION

Figure 1A:
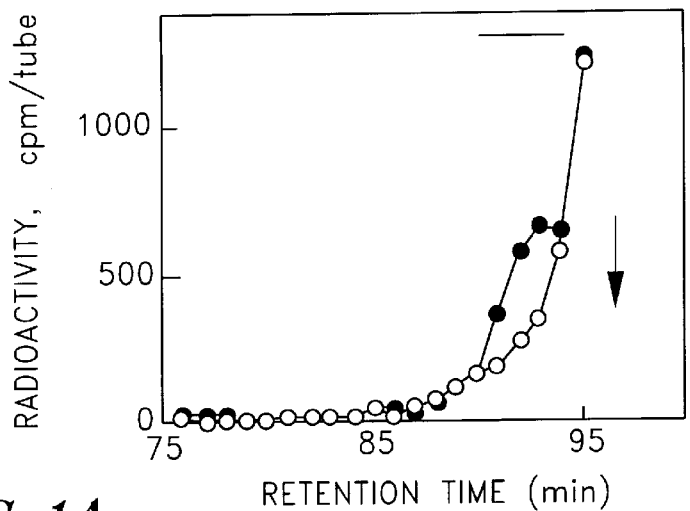
FIG. 1 shows results of Superdex 30 chromatography for $^{35}$S-labeled oligosaccharides produced from various lactosamine oligosaccharides.
Figure 1B:
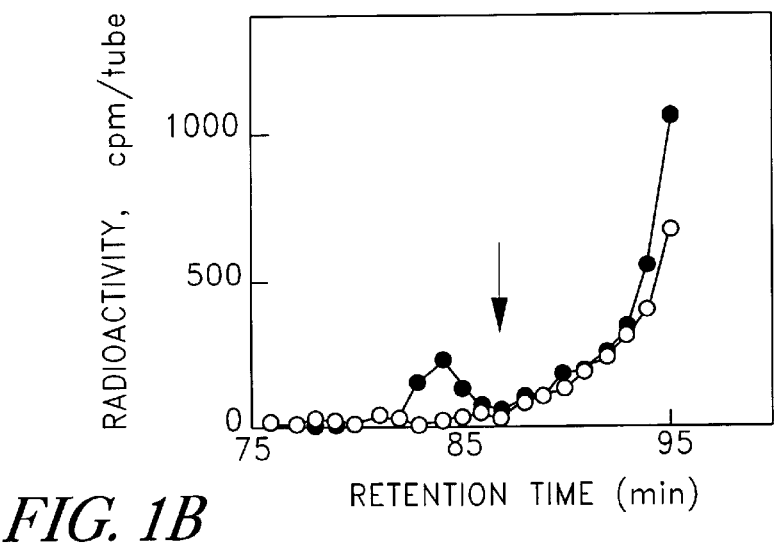
Figure 1C:
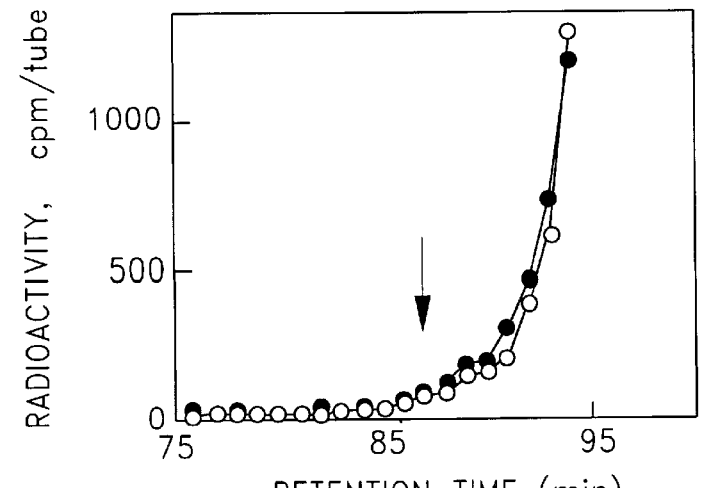
Figure 1D:
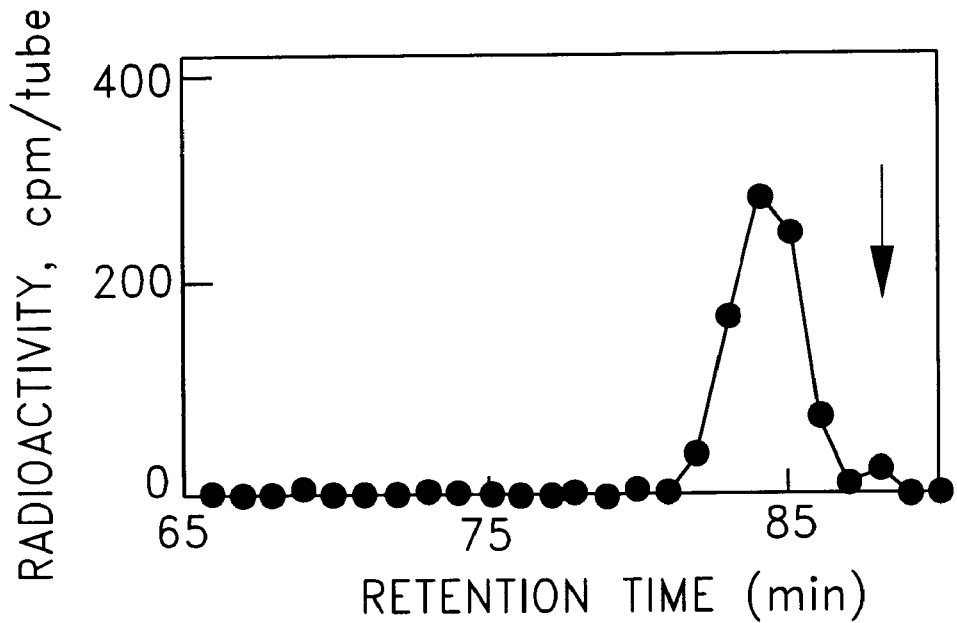
Figure 1E:
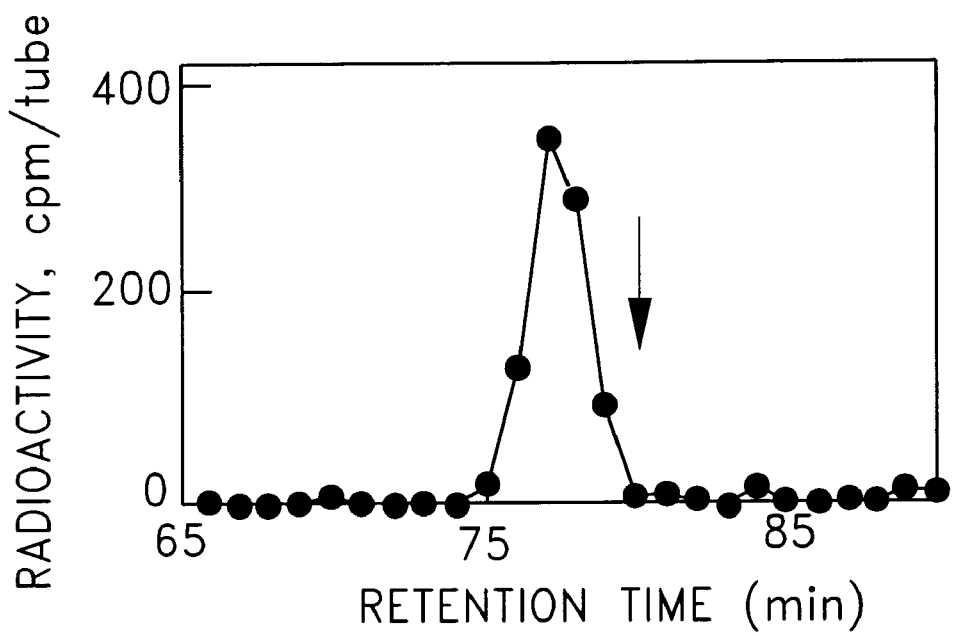
Figure 1F:
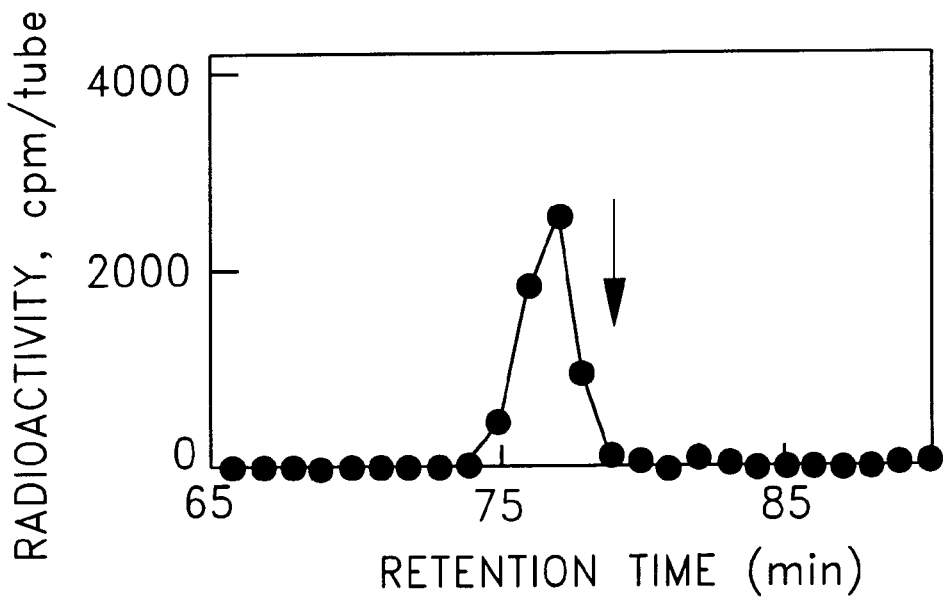
Figure 1G:
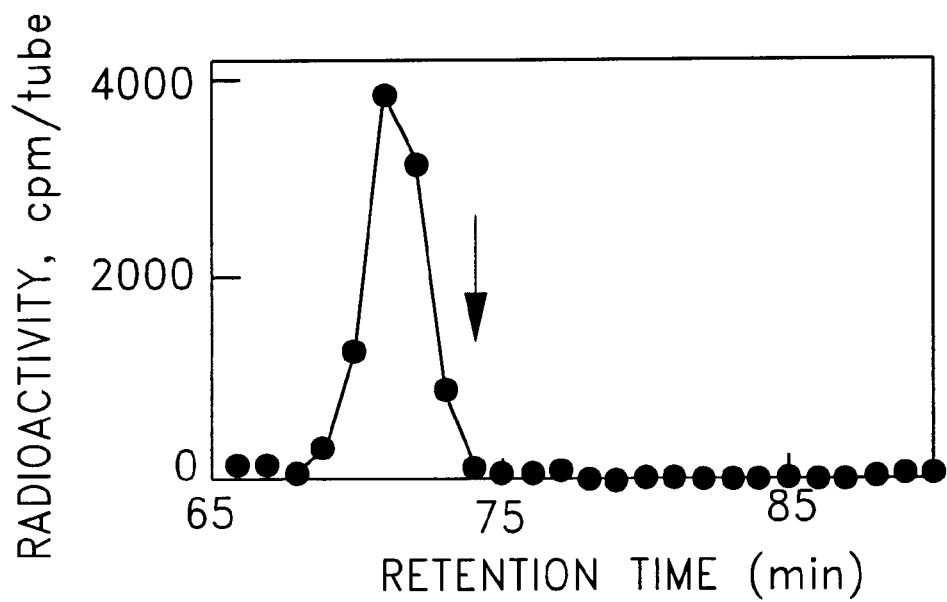

The sulfotransferase to be used for the method of the present invention is not specifically limited provided that the sulfotransferase transfers sulfate group to hydroxyl group at C-6 position of galactose residue in the lactosamine oligosaccharide. However, it is preferable to use a sulfotransferase transferring sulfate group to hydroxyl group at C-6 position of galactose residue of glycosaminoglycan. It is more preferable to use a sulfotransferase transferring sulfate group to hydroxyl group at C-6 position of galactose residue of keratan sulfate. It is especially preferable to use a sulfotransferase purified by the present inventors from a culture supernatant of chick chondrocyte cultivated in a serum-free medium (Habuchi, O., Matsui, Y., Kotoya, Y., Aoyama, Y., Yasuda, Y., and Noda, M. (1993), *J. Biol. Chem.*, 268, 21968–21974). The especially preferable sulfotransferase (hereinafter referred to as "chondroitin 6-sulfotransferase" or "C6ST", if necessary) has the following physical and chemical properties:

(1) action:

The sulfotransferase transfers sulfate group from a sulfate group donor to hydroxyl group at C-6 position of N-acetylgalactosamine residue or galactose residue of glycosaminoglycan.

(2) substrate specificity:

The sulfotransferase transfers sulfate group to chondroitin, chondroitin sulfate A, chondroitin sulfate C, and keratan sulfate, but sulfate group is not substantially transferred to chondroitin sulfate E, dermatan sulfate, and heparan sulfate. Preferably, the chondroitin originates from squid skin, the chondroitin sulfate A originates from whale cartilage, the chondroitin sulfate C originates from shark cartilage, and the keratan sulfate originates from bovine cornea. Preferably, the chondroitin sulfate E originates from squid cartilage, the dermatan sulfate originates from pig skin, and the heparan sulfate originates from bovine kidney. C6ST also transfers sulfate group to chondroitin sulfate originating from chick embryo cartilage.

(3) optimum reaction pH:

The sulfotransferase has an optimum reaction pH in the vicinity of 6.4.

(4) activation:

The activity of the sulfotransferase is increased by protamine or $MnCl_2$.

(5) molecular weight:

The sulfotransferase has a molecular weight of about 75 kilodaltons as estimated by sodium dodecyl sulfate-polyacrylamide gel electrophoresis under a reduced condition.

C6ST described above can be purified from cultured cells which express C6ST, such as chondrocyte, by combining methods for ordinarily purifying proteins and methods for ordinarily purifying sulfotransferases. Specifically, purification is preferably performed in accordance with a method described in *J. Biol. Chem.*, 268, (29), 21968–21974 (1993). Namely, substantially homogeneous C6ST can be obtained, for example, from a culture supernatant of chick embryo chondrocyte cultivated with a serum-free medium by means of affinity chromatography based on the use of Heparin-Sepharose CL-6B (commercially available from Pharmacia LKB Biotechnology), wheat germ agglutinin-agarose (commercially available from Seikagaku Corporation), and 3',5'-ADP-agarose (commercially available from Sigma).

The sulfotransferase can be also obtained by cloning a gene of the sulfotransferase usable in the present invention, introducing the cloned gene into an appropriate host, and expressing the gene in accordance with a known method. For example, DNA which codes for the sulfotransferase is isolated from a DNA library of an organism having the sulfotransferase usable in the present invention, by using an index of the sulfate group transfer activity specific to the hydroxyl group at C-6 position of galactose residue in the lactosamine oligosaccharide or glycosaminoglycan (preferably keratan sulfate). The isolated DNA is inserted into a vector by means of gene recombination, and the vector is then introduced into a host cell to perform expression therein. Thus the sulfotransferase can be obtained. Alternatively, cloning can be performed by preparing and using an antibody specific to the sulfotransferase. Alternatively, an N-terminal amino acid sequence of the sulfotransferase may be determined to perform cloning by using a probe of DNA having a nucleotide sequence deduced from the determined amino acid sequence. The expressed enzyme can be obtained in accordance with ordinary methods for enzyme extraction and purification. The extraction method specifically includes, for example, extraction based on the use of cell disruption, such as homogenization, ultrasonic treatment, osmotic shock, and freeze and thawing, extraction based on the use of a surfactant, and treating operations based on the use of a combination of the foregoing. The purification method specifically includes, for example, salting out based on the use of ammonium sulfate or sodium sulfate, centrifugation, dialysis, ultrafiltration, adsorption chromatography, ion exchange chromatography, hydrophobic chromatography, reverse phase chromatography, gel filtration, gel permeation chromatography, affinity chromatography, electrophoresis, and treatment operations based on the use of a combination of the foregoing.

A method for measuring the sulfotransferase activity and a method for inspecting the position of sulfate group transfer will be described in detail in Examples.

The lactosamine oligosaccharide usable in the method of the present invention is an oligosaccharide containing at least one lactosamine, such as lactosamine, an oligosaccharide containing at least one lactosamine, and an oligosaccharide comprising a basic backbone composed of a repeating structure of lactosamines. Among them, lactosamine itself, or the oligosaccharide comprising the basic backbone composed of the repeating structure of lactosamines is preferred. The oligosaccharide comprising the basic backbone composed of the repeating structure of lactosamines preferably comprises 2 to 10 units, more preferably 2 to 7 units, and especially preferably 2 units of the lactosamine structures.

In the case of the oligosaccharide containing at least one lactosamine, those in which lactosamine is present at the non-reducing end of the oligosaccharide are preferred. In the oligosaccharide containing at least one lactosamine, there is no special limitation concerning the linkage form between sugar residues other than lactosamine.

The amino sugar residue in lactosamine and the lactosamine oligosaccharide is glucosamine residue or N-acetylglucosamine residue. N-Acetylglucosamine residue is preferred.

As for the number of sugar residues, the lactosamine oligosaccharide preferably has about 2 to 20 sugar residues, more preferably has 2 to 15 sugar residues, and especially preferably has 2 to 5 sugar residues.

When the amino sugar residue in lactosamine is N-acetylglucosamine residue, the glycoside linkage from the galactose residue to the N-acetylglucosamine residue in lactosamine is preferably β-glycoside linkage, more preferably β1→4 glycoside linkage, i.e., Galβ1—4GlcNAc. When the basic backbone is the repeating structure of lactosamines, the glycoside linkage from the N-acetylglucosamine residue to the galactose residue (i.e., the glycoside linkage from lactosamine located on the non-reducing end side to lactosamine located on the reducing end side in the two adjacent lactosamines) is preferably β-glycoside linkage, more preferably β1→3 glycoside linkage, i.e., GlcNAcβ1—3Gal.

Lactosamine may have a sialic acid residue and/or a fucose residue. Namely, lactosamine may be sialylated and/or fucosylated. In the case of sialylated lactosamine, preferably the sialic acid residue is bound to the galactose residue through α-glycoside linkage, and more preferably the sialic acid residue is bound to the galactose residue through α2→3 glycoside linkage, i.e., SAα2—3Gal. The sialic acid includes, for example, N-acetylneuraminic acid and N-glycolylneuraminic acid. N-Acetylneuraminic acid is preferred. In the case of fucosylated lactosamine, preferably the fucose residue is bound to the N-acetylglucosamine residue through α-glycoside linkage, and more preferably the fucose residue is bound to the N-acetylglucosamine residue through α1→3 glycoside linkage, i.e., Fucα1—3GlcNAc.

It is allowable and preferable that the N-acetylglucosamine residue in lactosamine is sulfated. Oligosaccharides containing lactosamine with sulfated galactose residue may be used for the present invention provided that it contains at least one lactosamine having galactose residue which is not sulfated at hydroxyl group at C-6 position.

Of the lactosamine oligosaccharides, the lactosamine oligosaccharide which has a sialic acid residue at its non-reducing end, is apt to be sulfated to some extent as compared with the lactosamine oligosaccharide containing no sialic acid residue. Further, the lactosamine oligosaccharide which has a sulfated N-acetylglucosamine residue adjacent to the reducing-end side of a galactose residue that is not sulfated at hydroxyl group at C-6 position, is apt to be sulfated as compared with the lactosamine oligosaccharide which has a non-sulfated N-acetylglucosamine residue adjacent to the reducing-end side of the galactose residue that is not sulfated at hydroxyl group at C-6 position. Therefore, it is preferable to use those having a sulfated N-acetylglucosamine residue (preferably, sulfated at hydroxyl group at C-6 position) adjacent to the reducing-end side of the galactose residue that is not sulfated at hydroxyl group at C-6 position in the lactosamine oligosaccharide to which sulfate group is intended to be transferred (introduced).

Further, the lactosamine oligosaccharide which is not fucosylated, is apt to be sulfated as compared with the lactosamine oligosaccharide having a fucosylated N-acetylglucosamine residue. Especially, when the lactosamine oligosaccharide has a fucosylated N-acetylglucosamine residue adjacent to the reducing-end side of a galactose residue which is not sulfated at hydroxyl group at C-6 position (i.e., for example, Gal-(Fuc-)GalNAc), the galactose residue is difficult to be sulfated. Therefore, when it is intended to obtain a fucosylated sulfated lactosamine oligosaccharide, it is preferable that a non-fucosylated lactosamine oligosaccharide is used to obtain a sulfated lactosamine oligosaccharide which is then fucosylated by using fucosyltransferase.

It is noted that the lactosamine oligosaccharide to be used in the present invention can be appropriately selected by those skilled in the art depending on an objective sulfated lactosamine oligosaccharide.

Specifically, it is preferable to use, as the lactosamine oligosaccharide to be used in the present invention, for example, oligosaccharides represented by the following formulas:

Gal—GlcNAc—R (1)

Gal—GlcNAc(6S)—R (2)

SA—Gal—GlcNAc—R (3)

SA—Gal—GlcNAc(6S)—R (4)

In each of the foregoing formulas, R represents a hydrogen atom or a sugar chain containing 1 to 17 sugars, preferably R represents a hydrogen atom or a sugar chain containing 1 to 12 sugars, and especially preferably R represents a hydrogen atom or a sugar chain containing 1 to 2 sugars.

When R represents a sugar chain, R preferably includes a basic backbone composed of a repeating structure of Gal—GlcNAc. In this case, to the basic backbone, for example, any of a sialic acid residue, a fucose residue, and a sulfate group may be added.

It is more preferable to use, as the lactosamine oligosaccharide to be used in the present invention, oligosaccharides represented by the following formulas:

Gal—GlcNAc (5)

Gal—GlcNAc—Gal—GlcNAc (6)

Gal—GlcNAc(6S)—Gal(6S)—GlcNAc(6S) (7)

SA—Gal—GlcNAc (8)

SA—Gal—GlcNAc—Gal—GlcNAc (9)

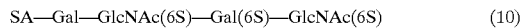
SA—Gal—GlcNAc(6S)—Gal(6S)—GlcNAc(6S) (10)

In each of the foregoing formulas (1) to (10), the sialic acid may be, for example, N-acetylneuraminic acid and N-glycolylneuraminic acid. N-Acetylneuraminic acid is preferred.

The source of the lactosamine oligosaccharides usable in the present invention is not specifically limited. Any lactosamine oligosaccharide obtained by any method can be used, including, for example, those extracted and purified from natural products, those produced by chemical synthesis, those produced by chemical degradation, those produced by using sugar-degrading enzyme, and those produced by using sugar transferase. Those commercially available may be used.

Specifically, in the case of production by using the sugar-degrading enzyme, for example, the lactosamine oligosaccharide usable in the present invention can be produced by degrading keratan sulfate, preferably keratan sulfate obtainable from cartilage, bone, cornea or the like of cartilagenous fish such as shark or mammalian such as whale and bovine, with, for example, an endo-β-galactosidase type enzyme (for example, endo-β-galactosidase and keratanase; any of them is commercially available from Seikagaku Corporation) or an endo-β-glucosaminidase type enzyme (for example, keratanase II; commercially available from Seikagaku Corporation).

The sulfotransferase which transfers sulfate group to hydroxyl group at C-6 position of the galactose residue in lactosamine in the lactosamine oligosaccharide, is allowed to act on the lactosamine oligosaccharide in the co-presence of a sulfate group donor. Thus the sulfate group is transferred from the sulfate group donor to hydroxyl group at C-6 position of the galactose residue in lactosamine in the lactosamine oligosaccharide, and sulfated lactosamine oligosaccharide is produced. Preferred sulfated lactosamine oligosaccharides obtainable by the method of the present invention include, for example, sulfated lactosamine oligosaccharides represented by the following formulas:

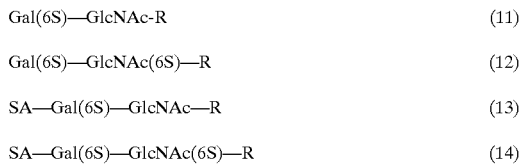

| Gal(6S)—GlcNAc-R | (11) |
| Gal(6S)—GlcNAc(6S)—R | (12) |
| SA—Gal(6S)—GlcNAc—R | (13) |
| SA—Gal(6S)—GlcNAc(6S)—R | (14) |

In each of the foregoing formulas, R represents a hydrogen atom or a sugar chain containing 1 to 17 sugars, preferably R represents a hydrogen atom or a sugar chain containing 1 to 12 sugars, and especially preferably R represents a hydrogen atom or a sugar chain containing 1 to 2 sugars.

When R represents a sugar chain, R preferably has a basic backbone composed of a repeating structure of Gal—GlcNAc. In this case, to the basic backbone, for example, a sialic acid residue, any of a fucose residue, and a sulfate group may be added.

Of the foregoing, it is preferable to use sulfated lactosamine oligosaccharides represented by the following formulas:

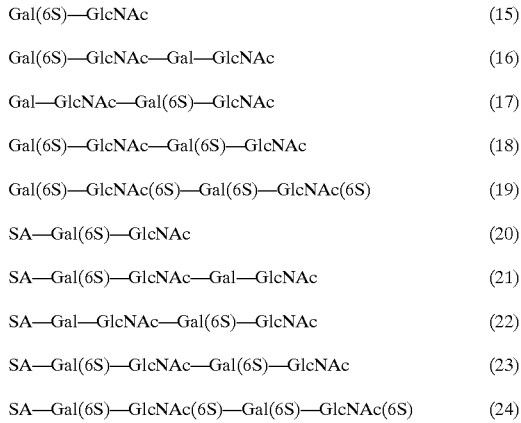

| Gal(6S)—GlcNAc | (15) |
| Gal(6S)—GlcNAc—Gal—GlcNAc | (16) |
| Gal—GlcNAc—Gal(6S)—GlcNAc | (17) |
| Gal(6S)—GlcNAc—Gal(6S)—GlcNAc | (18) |
| Gal(6S)—GlcNAc(6S)—Gal(6S)—GlcNAc(6S) | (19) |
| SA—Gal(6S)—GlcNAc | (20) |
| SA—Gal(6S)—GlcNAc—Gal—GlcNAc | (21) |
| SA—Gal—GlcNAc—Gal(6S)—GlcNAc | (22) |
| SA—Gal(6S)—GlcNAc—Gal(6S)—GlcNAc | (23) |
| SA—Gal(6S)—GlcNAc(6S)—Gal(6S)—GlcNAc(6S) | (24) |

In each of the foregoing formulas (11) to (24), the sialic acid may be, for example, N-acetylneuraminic acid and N-glycolylneuraminic acid. N-Acetylneuraminic acid is preferred.

The sulfated lactosamine oligosaccharide (11) is obtained from the lactosamine oligosaccharide (1). The sulfated lactosamine oligosaccharide (12) is obtained from the lactosamine oligosaccharide (2). The sulfated lactosamine oligosaccharide (13) is obtained from the lactosamine oligosaccharide (3). The sulfated lactosamine oligosaccharide (14) is obtained from the lactosamine oligosaccharide (4). The sulfated lactosamine oligosaccharide (15) is obtained from the lactosamine oligosaccharide (5). The sulfated lactosamine oligosaccharides (16), (17), (18) are obtained from the lactosamine oligosaccharide (6). The sulfated lactosamine oligosaccharide (19) is obtained from the lactosamine oligosaccharide (7). The sulfated lactosamine oligosaccharide (20) is obtained from the lactosamine oligosaccharide (8). The sulfated lactosamine oligosaccharides (21), (22), (23) are obtained from the lactosamine oligosaccharide (9). The sulfated lactosamine oligosaccharide (24) is obtained from the lactosamine oligosaccharide (10).

The reaction in which the sulfotransferase transferring sulfate group to hydroxyl group at C-6 position of the galactose residue in the lactosamine oligosaccharide is allowed to act on the lactosamine oligosaccharide, can be performed by allowing the sulfotransferase, a sulfate group donor, and the lactosamine oligosaccharide to co-exist. In this reaction, pH is not specifically limited provided that the activity of the sulfotransferase is maintained. However, it is preferable to perform the reaction under a pH condition in the vicinity of an optimum reaction pH of the sulfotransferase. More preferably, the reaction is performed in a buffer having a buffering action at the foregoing pH. The temperature is not specifically limited as well provided that the activity of the sulfotransferase is maintained. However, it is preferable to perform the reaction in the vicinity of an optimum temperature for the sulfotransferase. When a substance which serves to increase the activity of the sulfotransferase, is available, the substance may be added. The reaction time can be appropriately determined by those skilled in the art depending on the amounts of the lactosamine oligosaccharide, the sulfate group donor, and the sulfotransferase to be used, and other reaction conditions. When C6ST is used as the sulfotransferase, for example, the reaction is preferably performed in the vicinity of pH 6.4 at a temperature in the vicinity of 30 to 40° C., especially in the vicinity of 37° C. Further, protamine and/or $MnCl_2$ may be allowed to co-exist during the reaction.

The sulfate group donor which is used for the reaction to allow the sulfotransferase to act, preferably includes activated sulfate (3'-phosphoadenosine 5'-phosphosulfate; hereinafter referred to as "PAPS").

In the case of production in a small amount, it is sufficient that the sulfotransferase which transfers the sulfate group to hydroxyl group at C-6 position of the galactose residue in the lactosamine oligosaccharide, is allowed to exist and make the action of the enzyme in the co-presence of the lactosamine oligosaccharide and the sulfate group donor. However, in the case of production in a large amount, it is possible to allow the enzyme to act continuously by using, for example, immobilized enzyme obtained by binding the sulfotransferase to an appropriate solid phase (beads or the like), or by using a membrane-type reactor based on the use of ultrafiltration membrane, dialysis membrane or the like. Alternatively, a bioreactor may be combined and used for reproducing (synthesizing) the sulfate group donor.

In order to recover the sulfated lactosamine oligosaccharide from the reaction solution, it is possible to use ordinary methods for separation and purification of sugar chains. The sulfated lactosamine oligosaccharide can be recovered, for example, by means of operation including, for example, adsorption chromatography, anion exchange chromatography, hydrophobic chromatography, gel filtration, gel permeation chromatography, paper electrophoresis, paper chromatography, fractionation with organic solvent (preferably, for example, alcohol and acetone), and a combination of the foregoing. However, there is no limitation thereto. For example, the sulfated lactosamine oligosaccharide can be recovered by adding NaCl to a reaction solution containing the sulfated lactosamine oligosaccharide produced in accordance with the method of the present invention so that the concentration of NaCl is, for example, about 0.2 M, applying an obtained solution to an anion exchange column to remove non-adsorbed fractions, and eluting an adsorbed fraction with, for example, NaCl at about 2.5 M. In this procedure, the adsorbed fraction (sulfated lactosamine oligosaccharide) may be eluted with a concentration gradient of NaCl. The condition for the elution and other parameters can be appropriately determined by those skilled in the art.

The obtained sulfated lactosamine oligosaccharide can be utilized as an intermediate for producing the basic backbone of the sugar chain of GlyCAM-1. For this purpose, when the sulfated lactosamine oligosaccharide to be used has a non-sialylated galactose residue (for example, those represented by the foregoing formulas (11), (12), (15) to (19)), sialic acid can be added to the galactose residue by using sialyltransferase. On the other hand, when the sulfated lactosamine oligosaccharide to be used has a non-fucosylated N-acetylglucosamine residue, fucose may be added thereto by using fucosyltransferase.

GlyCAM-1 and the backbone of the sugar chain thereof are expected to be utilized as anti-inflammatory agents.

EXAMPLES

The present invention will be explained more specifically below with reference to Examples. However, Examples are only illustrative of the present invention, to which the present invention is not limited.

At first, available sources of reagents used in Examples, exemplary preparation of chondroitin 6-sulfotransferase (C6ST), and procedures used in Examples will be described below.

(1) Available Sources of Reagents $H_2^{35}SO_4$: du Pont/NEN;
[$^3$H]NaBH$_4$ (16.3 GBq/mmol) (Amersham);
PAPS (Sigma);
Fast Desalting Column HR 10/10 (Pharmacia);
Hiload Superdex 30 16/60 (Pharmacia);
Chondroitinase ACII (Seikagaku Corporation);
Neuraminidase originating from Streptococcus (Seikagaku Corporation);
β-Galactosidase originating from Streptococcus (Seikagaku Corporation);
Partisil 10-SAX column (Whatman);
NeuAcα2—3Galβ1—4(Fucα1-3)GlcNAc (SLe$^x$) (Funakoshi);
NeuAcα2—3Galβ1—4GlcNAc (SLN) (Funakoshi);
Galβ1—4GlcNAc (LN) (Funakoshi);
Keratan sulfate originating from bovine cornea (Seikagaku Corporation);
NeuAcα2—3Galβ1—4GlcNAc(6S) β1—3Gal(6S)β1—4GlcNAc(6S) (SL2L4) (Seikagaku Corporation);
NeuAcα2—3Galβ1—4GlcNAcβ1—3Galβ1—4GlcNAc (SL1L1) (Seikagaku Corporation);
Gal⊖1—4GlcNAcβ1—3Galβ1—4GlcNAc (L1L1) (Seikagaku Corporation);
[$^{35}$S]PAPS (obtained in accordance with Delfert, D. M. and Conrad, H. E. (1985), *Anal, Biochem.*, 148, 303–310);
[$^3$H]Gal(6S)β1—4AManR and [$^3$H]Galβ1—4AManR (6S) (herein referred to as "standard sulfated disaccharides") as well, wherein AManR means alditol of 2,5-anhydro-D-mannose) to be used as standard substances for high-performance liquid chromatography (HPLC) based on the use of Partisil 10-SAX column were obtained by allowing keratan sulfate to undergo N-deacetylation, deaminative cleavage, and reduction with NaB$^3$H$_4$ to prepare [$^3$H]Gal (6S)β1—4AManR(6S) which was then subjected to partial acid hydrolysis (0.1 M HCl, 100° C., 40 minutes) (see Shaklee, P. N. and Conrad, H. E. (1986), *Biochem. J.*, 235, 225–236). [$^3$H]Gal(6S)β1—4AManR and [$^3$H]Galβ1—4AManR(6S) were purified from products obtained by the hydrolysis described above, by means of paper chromatography (developing solvent: 1-butanol/acetic acid/1 M NH$_3$= 3:2:1 (v/v/v) and paper electrophoresis;

Galβ1—4GlcNAc(6S)β1—3Gal(6S)β1—4GlcNAc(6S) (L2L4) was prepared by digesting SL2L4 with neuraminidase. Products obtained by the neuraminidase digestion were applied to a column of Partisil 10-SAX, followed by elution with a concentration gradient of KH$_2$PO$_4$ ranging from 25 mM to 500 mM. A peak fraction eluted from the column was further purified by using gel filtration chromatography (Superdex 30 chromatography), followed by lyophilization.

(2) Preparation of Chondroitin 6-sulfotransferase (C6ST)

Chondroitin 6-sulfotransferase was purified from a serum-free medium obtained after cultivation of chick chondrocyte therein, in accordance with a known method (Habuchi, O., Matsui, Y., Kotoya, Y., Aoyama, Y., Yasuda, Y., and Noda, M. (1993), *J. Biol. Chem.*, 268, 21968–21974).

Chondrocytes of chick embryo were inoculated in a culture dish to give a concentration of 5.6×10$^4$/dish, and they were cultured for 11 days under a condition of 7% CO$_2$ and 93% air at 38° C. in Dulbecco's Modified Eagle's Medium (DMEM) adjusted at pH 7.0, containing 2 g/L of D-glucose, 100 units/ml of penicillin, 50 μg/ml of streptomycin, and 10% fetal bovine serum (FBS). The medium was replaced with a fresh medium at pH 7.4 on 2nd, 4th, 7th, 9th, and 10th days after the start of the cultivation. A medium containing 10% heat-inactivated serum prepared by heating FBS at 60° C. for 60 minutes was used on 10th day. The cells grew on 11th day up to a concentration of 5.0×10$^6$ cells/dish. After that, Cosmedium-001 (purchased from CosmoBio) supplemented with 50 μg/ml of sodium ascorbate was used to continue cultivation for 10 days while exchanging the medium every day.

The used medium of Cosmedium-001 was collected, and the collected medium was centrifuged at 10,000× g for 10 minutes. An obtained supernatant was adjusted to have a composition comprising 10 mM Tris-HCl, pH 7.2, 0.1% Triton X-100, 20 mM MgCl$_2$, 10 mM 2-mercaptoethanol, and 20% glycerol.

The culture supernatant was applied to a column of Heparin-Sepharose CL-6B (produced by Pharmacia LKB Biotechnology, 2.2×28 cm) equilibrated with buffer A (10 mM Tris-HCl, pH 7.2, 0.1% Triton X-100, 20 mM MgCl$_2$, 2 mM CaCl$_2$, 10 mM 2-mercaptoethanol, and 20% glycerol) containing 0.15 M NaCl. The column was washed with buffer A containing 0.15 M NaCl, followed by elution with buffer A containing 0.45 M NaCl to perform fractionation.

Fractions having the sulfotransferase activity were collected, and an obtained collected fraction was applied to a column of wheat germ agglutinin-agarose (produced by Seikagaku Corporation, 1.2×15 cm) equilibrated with buffer A containing 0.15 M NaCl. The column was washed with buffer A (200 ml) containing 0.15 M NaCl, followed by elution with buffer A (200 ml) containing 0.15 M NaCl and 0.3 M N-acetylglucosamine. Eluted fractions were collected, and an obtained collected fraction was dialyzed against buffer A containing 0.05 M NaCl.

The obtained fraction was applied to a column of 3', 5'-ADP-agarose (produced by Sigma, 1.2×11.8 cm, 1.9 μmol 3', 5'-ADP/ml gel) equilibrated with buffer A containing 0.05 M NaCl. The column was washed with buffer A (150 ml) containing 0.05 M NaCl, followed by elution with a linear gradient based on buffer A (300 ml) containing 0.05 M NaCl and further containing 0 to 0.2 mM 3', 5'-ADP. Fractions having the sulfotransferase activity were collected, and an obtained collected fraction was dialyzed against buffer A containing 1 M NaCl, and then dialyzed against buffer A containing 0.05 M NaCl.

In the purification steps, the sulfotransferase activity was measured as follows. The reaction solution had the following composition. Namely, the reaction solution (50 $\mu$l) contained 2.5 $\mu$mol of imidazol-HCl, pH 6.8, 1.25 $\mu$g of protamine hydrochloride, 0.1 $\mu$mol of dithiothreitol, 25 nmol (as an amount of glucuronic acid) of chondroitin (produced by Seikagaku Corporation), 50 pmol of [$^{35}$S]PAPS (adenosine 3'-phosphate, 5'-phosphosulfate), and the enzyme.

The activity was measured for various glycosaminoglycans as the substrate, by using 25 nmol of glycosaminoglycans (as an amount of galactosamine for chondroitin sulfate and dermatan sulfate, or as an amount of glucosamine for heparan sulfate and keratan sulfate) in place of chondroitin.

The reaction solution was incubated at 37° C. for 20 minutes in a reaction tube, and then the reaction was terminated by immersing the reaction tube in boiling water for 1 minute. After the termination of the reaction, 0.1 $\mu$mol of chondroitin sulfate A (as an amount of glucuronic acid) was added as a carrier, and three volumes of ethanol containing 1.3% potassium acetate was added thereto to precipitate $^{35}$S-labeled polysaccharide. The mixture was centrifuged at 10,000× g for 10 minutes to obtain a precipitate which was then dissolved in 70 $\mu$l of water. An aliquot (50 $\mu$l) of the obtained solution was injected into a desalting column equilibrated with 0.1 M NH$_4$HCO$_3$, and eluted fractions containing the $^{35}$S-labeled polysaccharide were collected. To an aliquot (200 $\mu$l) of an obtained collected fraction, 1 ml of a scintillation cocktail (Clearsol, produced by nacalai tesque) was added to measure $^{35}$S-radioactivity. Thus incorporation of $^{35}$S into the polysaccharide was measured.

An aliquot (400 $\mu$l) was dispensed from the residual solution, to which 800 $\mu$l of ethanol containing 1.3% potassium acetate was added, followed by mixing. The mixture was placed on ice for 30 minutes, followed by centrifugation at 10,000× g for 10 minutes to precipitate the $^{35}$S-labeled polysaccharide. The precipitate was dissolved in 25 $\mu$l of a buffer containing 0.1 mg/ml of BSA, 0.05 M Tris-acetate, pH 7.5, and 10 milliunits of chondroitinase ACII (originating from *Arthrobacter aurescens*, produced by Seikagaku Corporation) to perform a reaction at 37° C. for 2 hours. The solution after the reaction was spotted onto Whatman No. 1 filter paper together with 2-acetamido-2-deoxy-3-O-($\beta$-D-gluco-4-enopyranosyluronic acid)-6-O-sulfo-D-galactose ($\Delta$Di-6S) and 2-acetamido-2-deoxy-3-O-($\beta$-D-gluco-4-enopyranosyluronic acid)-4-O-sulfo-D-galactose ($\Delta$Di-4S) (each 0.1 $\mu$mol, each produced by Seikagaku Corporation), followed by development for 20 hours with 1-butanol/acetic acid/1 M ammonium hydroxide (2:3:1 (V/V/V)).

Positions of $\Delta$Di-6S and $\Delta$Di-4S were inspected by using an ultraviolet lamp respectively. Portions corresponding to them were excised from the filter paper respectively, and were then placed in a scintillator prepared by dissolving 5 g of diphenyloxazole and 0.25 g of dimethyl-1,4-bis(2-(5-phenyloxazole))benzene in 1 L of toluene to measure radioactivity. As for a sample obtained by digestion with chondroitinase ACII, the radioactivity remained on the starting point on the filter paper was not more than 1% of the spotted radioactivity. According to incorporation of $^{35}$S into $\Delta$Di-6S and $\Delta$Di-4S, activities of chondroitin 6-sulfotransferase and chondroitin 4-sulfotransferase were calculated respectively. The activity to catalyze transfer of 1 pmol sulfate group/minute was defined as 1 unit. As a result, the specific activity of chondroitin 6-sulfotransferase was 4.3×10$^5$ units/mg, and the ratio of activities of chondroitin 4-sulfotransferase/chondroitin 6-sulfotransferase was 0.02.

C6ST purified as described above formed a single band on sodium dodecyl sulfate-polyacrylamide gel electrophoresis (SDS-PAGE) under a reduced condition, and its molecular weight was determined to be about 75,000. The molecular weight was about 160,000 as a result of measurement by using Superose 12 HR 10/30 gel filtration chromatography (eluent: 10 mM Tris-HCl, pH 7.2, 2 M NaCl, 20 mM MgCl$_2$, 2 mM CaCl$_2$, 0.1% Triton X-100, and 20% glycerol). Therefore, it was suggested that C6ST formed a dimer in the presence of 2 M NaCl.

The sulfotransferase activity was measured for a variety of substrates. As a result, it has been demonstrated that C6ST obtained as described above transfers the sulfate group to chondroitin originating from squid skin, chondroitin sulfate originating from chick embryo cartilage, chondroitin sulfate A originating from whale cartilage, chondroitin sulfate C originating from shark cartilage, and keratan sulfate originating from bovine cornea, but the sulfate group is only scarcely transferred to chondroitin sulfate E originating from squid cartilage, dermatan sulfate originating from pig skin, and heparan sulfate originating from bovine kidney. It has been confirmed by the present inventors that C6ST transfers the sulfate group to hydroxyl group at C-6 position of galactose residue in the case of keratan sulfate.

The activity of C6ST of the present invention was increased by protamine and MnCl$_2$ respectively.

C6ST had an optimum reaction pH of about 6.4 in the measuring system described above.

(3) Methods Used in Examples (3-1) Degradation with Neuraminidase and $\beta$-galactosidase Digestion with neuraminidase was performed by using a reaction mixture (25 $\mu$l) containing an oligosaccharide to which $^{35}$SO$_4$ had been transferred, 2.5 $\mu$mol of potassium acetate buffer (pH 6.5), 0.25 $\mu$mol of CaCl$_2$, and 10 mU of neuraminidase (see Kiyohara, T. et al. (1974), *Arch. Biochem. Biophys.*, 164, 575–582). The reaction mixture was incubated at 37° C. for 60 minutes.

Digestion with $\beta$-galactosidase was performed by using a reaction mixture (50 $\mu$l) containing an oligosaccharide from which sialic acid had been removed and to which $^{35}$SO$_4$ had been transferred, 50 nmol of L1L1 or L2L4, 2.5 $\mu$mol of sodium acetate buffer (pH 5.5), and 10 mU of $\beta$-galactosidase (see Kiyohara, T. et al. (1976), *J. Biochem.*, 80, 9–17). The reaction mixture was incubated at 37° C. for 60 minutes.

(3-2) Gel Filtration Chromatography and Paper Electrophoresis

Gel filtration chromatography was performed by using a column of Hiload Superdex 30 16/60. The column was equilibrated with 0.2 M NH$_4$HCO3, and the flow rate was 1 ml/minute. Fractions of 1 ml or 0.5 ml were collected, which were then mixed with 4 ml of Clearsol (produced by nacalai tesque) to measure the radioactivity. The oligosaccharide was monitored on the basis of absorbance at 210 nm.

Paper electrophoresis was performed at 30 V/cm for 40 minutes or 80 minutes by using Whatman No. 3 filter paper (2.5×57 cm) in pyridine/acetic acid/water (1:10:400 (v/v/v), pH 4). After the paper electrophoresis, the filter paper was dried and cut into small pieces of 1.25 cm and the radioactivity was analyzed by means of liquid scintillation counting by using a scintillation solution containing 5 g of diphenyloxazole and 0.25 g of dimethyl-1,4-bis(2-(5-phenyloxazole))benzene in 1 L of toluene.

(3-3) Quantitative Determination for Glucosamine and Sialic Acid

The glucosamine content in oligosaccharide was quantitatively determined in accordance with a partially modified Elson-Morgan method described by Strominger et al. (Strominger, J. L. et al. (1959), *J. Biol. Chem.*, 234, 3263–3268), after hydrolyzing glycosaminoglycan in 6 M HCl at 100° C. for 4 hours.

Sialic acid was quantitatively determined in accordance with the thiobarbituric acid method (Aminoff, D. (1961), *Biochem. J.*, 81, 384–392), after performing hydrolysis in 0.1 M $H_2SO_4$ at 80° C. for 60 minutes.

Example 1

Transfer Reaction of Sulfate Group to Various Lactosamine Oligosaccharides by Using Sulfotransferase Structures and abbreviations of lactosamine oligosaccharides used herein are shown in Table 1.

Specifically, the transfer reaction of sulfate group ($^{35}SO4$ was used as sulfate group in order to confirm sulfation) to various lactosamine oligosaccharides by using sulfotransferase was performed in accordance with the following method. A standard reaction mixture was a solution containing 2.5 µmol of imidazole-HCl (pH 6.8), 0.25 µmol of $CaCl_2$, 0.1 µmol of dithiothreitol, 0.025 µmol of various lactosamine oligosaccharides, 25 pmol of [$^{35}S$]PAPS (about $2.5 \times 10^5$ cpm), and 0.09 µg of purified chondroitin 6-sulfotransferase in a final volume of 50 µl. The reaction mixture was subjected to the reaction at 37° C. for 60 minutes in a reaction tube. The reaction was terminated by immersing the reaction tube in boiling water for 1 minute. After the termination of the reaction, lactosamine oligosaccharide (sulfated lactosamine oligosaccharide) to which $^{35}SO_4$ had been transferred was separated from free $^{35}SO_4$ and [$^{35}S$]PAPS by means of gel filtration chromatography. A fraction (1 ml) was collected to measure the radioactivity.

Results are shown in FIG. 1. A result obtained by using LN as the lactosamine oligosaccharide is shown in A, a result obtained by using SLN is shown in B, a result obtained by using $SLe^x$ is shown in C, a result obtained by using L1L1 is shown in D, a result obtained by using SL1L1 is shown in E, a result obtained by using L2L4 is shown in F, and a result obtained by using SL2L4 is shown in G. In A to C, open circles indicate the results obtained by using purified chondroitin 6-sulfotransferase having been heat-inactivated by means of a treatment at 100° C. for 2 minutes (control), and closed circles indicate the results obtained by using intact purified chondroitin 6-sulfotransferase. In D to G, closed circles indicate values obtained by subtracting values obtained by using purified chondroitin 6-sulfotransferase having been heat-inactivated by a treatment at 100° C. for 2 minutes (control), from values obtained by using intact purified chondroitin 6-sulfotransferase.

The retention time of the sulfated lactosamine oligosaccharide was faster by 2 to 3 minutes than the retention time (indicated by arrows shown in FIG. 1) of the lactosamine oligosaccharide used (lactosamine oligosaccharide before sulfation (acceptor)). When $SLe^x$ was used as the acceptor, it was predicted that sulfated $SLe^x$ had a retention time of 83 to 84 minutes. However, no radioactivity was detected in the vicinity of the predicted retention time. Incorporation of sulfate group into the lactosamine oligosaccharides is shown in Table 1. A peak of sulfated LN partially overlapped with those of free $^{35}SO_4$ and [$^{35}S$]PAPS. A radioactivity peak (indicated by a horizontal bar in FIG. 1A) of a product produced from LN was subjected to paper electrophoresis. As a result, the sulfated LN was separated from $^{35}SO_4$ and [$^{35}S$]PAPS. Therefore, incorporation of sulfate group ($^{35}SO_4$) into LN was calculated after the paper electrophoresis.

TABLE 1

| Abbreviation | Structure of oligosaccharide | Incorporation of $^{25}S$*1 |
| --- | --- | --- |
| LN | Galβ1—4GlcNAc | 0.012 |
| SLN | NeuAcα2—3Galβ1—4GlcNAc | 0.022 |
| $SLe^x$ | NeuAcα2—3Galβ1—4(Fucα1–3)GlcNAc | —*2 |
| L1L1 | Galβ1—4GlcNAcβ1—3Galβ1—4GlcNAc | 0.031 |
| SL1L1 | NeuAcα2—3Galβ1—4GlcNAcβ1—3Galβ1—4GlcNAc | 0.034 |
| L2L4 | Galβ1—4GlcNAc(6S)β1—3Gal(6S)β1—4GlcNAc(6S) | 0.29 |
| SL2L4 | NeuAcα2—3Galβ1—4GlcNAc(6S)β1—3Gal(6S)β1—4GlcNAc(6S) | 0.48 |

*1 pmol/minute/µg protein
*2 this symbol indicates no detection.

According to Table 1, transfer (incorporation) of sulfate group was not detected for $SLe^x$, while incorporation of sulfate group was observed for LN, SLN, L1L1, SL1L1, L2L4, and SL2L4. The amounts of incorporation into oligosaccharides having sialic acid at their non-reducing ends were somewhat larger than the amounts of incorporation into oligosaccharides having no sialic acid. Among these oligosaccharides, the maximum incorporation of sulfate group was observed in SL2L4. According to this fact, it is suggested that the sulfate group (6S) of the GlcNAc(6S) residue adjacent to the reducing-end side of the Gal residue increases the incorporation of sulfate group into the Gal residue. No incorporation of sulfate group was observed for $SLe^x$. Accordingly, it has been suggested that the Fuc residue linked to the GlcNAc residue adjacent to the reducing-end side of the Gal residue restrains the transfer reaction of sulfate group to the Gal residue by the aid of chondroitin 6-sulfotransferase.

Example 2

Investigation of Position of Sulfation in Lactosamine Oligosaccharide

In order to determine the position of transfer of sulfate group in the sulfated lactosamine oligosaccharide, sulfated SLN was subjected to reactions in an order of digestion with neuraminidase, N-deacetylation, deamination, and reduction with NaBH$_4$. An obtained degraded product was compared with the standard sulfated disaccharides. Specifically, the procedure was as follows.

SLN including transferred sulfate group ($^{35}$SO$_4$) (sulfated SLN) was prepared in the same manner as the transfer reaction described in Example 1 except that the concentration of [$^{35}$S]PAPS in the reaction mixture was increased 4-fold, and the incubation was performed for 16 hours. SLN including transferred $^{35}$SO$_4$ was applied to a column of gel filtration (Superdex 30 column). Sulfated SLN eluted from the column was lyophilized, purified by means of paper electrophoresis, and digested with neuraminidase in the same manner as described above.

The sample obtained after the neuraminidase digestion was subjected to separation by means of paper electrophoresis, followed by hydrazinolysis. The hydrazinolysis was performed in accordance with a method described by Guo, Y. and Conrad, H. E. (1989), *Anal. Biochem.*, 176, 96–104. The desialylated sample was placed into a vial having a volume of 100 µl (Reacti-Vial, produced by Pierce), dried in N$_2$ stream, and finally dissolved in 100 µl of 70% hydrazine containing 0.2 mg of hydrazine sulfate. The sample was covered with a cap, followed by being left to stand in a sand bath at 95° C. for 6 hours. The sample was cooled, dried in N$_2$ stream, dissolved in a small amount of water, and lyophilized to remove almost all hydrazine.

A deacetylated material thus obtained was purified by means of gel filtration chromatography and paper electrophoresis, followed by deamination with nitrous acid. Specifically, the deamination was performed as follows in accordance with a method described by Shaklee, P. N. and Conrad, H. E. (1986), *Biochem. J.*, 235, 225–236. Namely, the deacetylated material was dissolved in 20 µl of HNO$_2$ solution (pH 4) (prepared by mixing 250 µl of 5.5 M NaNO$_2$ and 100 µl of 1 M H$_2$SO$_4$). The sample was left to stand at room temperature for 30 minutes, and then cooled in ice. pH was adjusted to be 8.5 with 7 µl of 1 M Na$_2$CO$_3$. The sample was mixed with 10 µl of 0.5 M NaBH$_4$ dissolved in 0.2 M Na$_2$CO$_3$ (pH 10.2) (reduction with NaBH$_4$). Excessive NaBH$_4$ was degraded by adding 5 µl of 3 M acetic acid. The sample was dried in N$_2$ stream, dissolved in water again, and dried again. Finally, the sample was dissolved in 60 µl of water, and purified by means of gel filtration chromatography and paper electrophoresis.

Reaction products obtained in the foregoing respective steps were subjected to paper electrophoresis to measure radioactivity. Results are shown in FIG. 2. In FIG. 2, A shows a result for SLN including transferred $^{35}$SO$_4$, B shows a result for a reaction product obtained by digestion of a peak fraction shown in A with neuraminidase, C shows a result for a reaction product obtained by hydrazinolysis (N-deacetylation) of a peak fraction shown in B, and D shows a result for a reaction product obtained by deamination of a fraction corresponding to a slowly moving peak (indicated by a horizontal bar in FIG. 2C) shown in C, followed by reduction with NaBH$_4$. The results were obtained by performing electrophoresis for 40 minutes (A and B) or for 80 minutes (C and D).

Figure 2A:
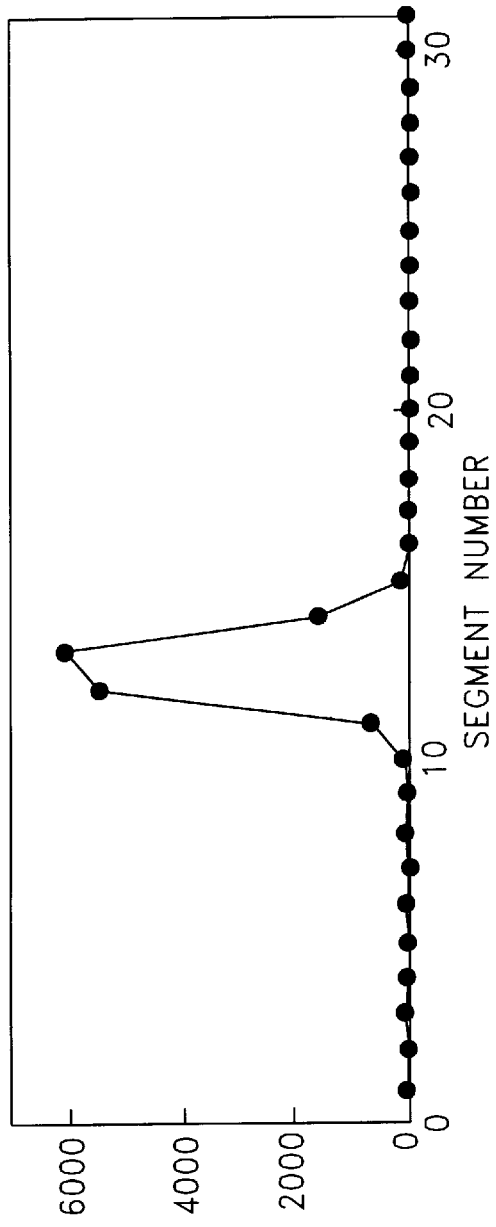
FIG. 2 shows results of paper electrophoresis for reaction products obtained from NeuAcα2—3Galβ1—4GlcNAc (SLN) after digestion with neuraminidase, N-deacetylation, deamination, and reduction with NaBH$_4$.
Figure 2B:
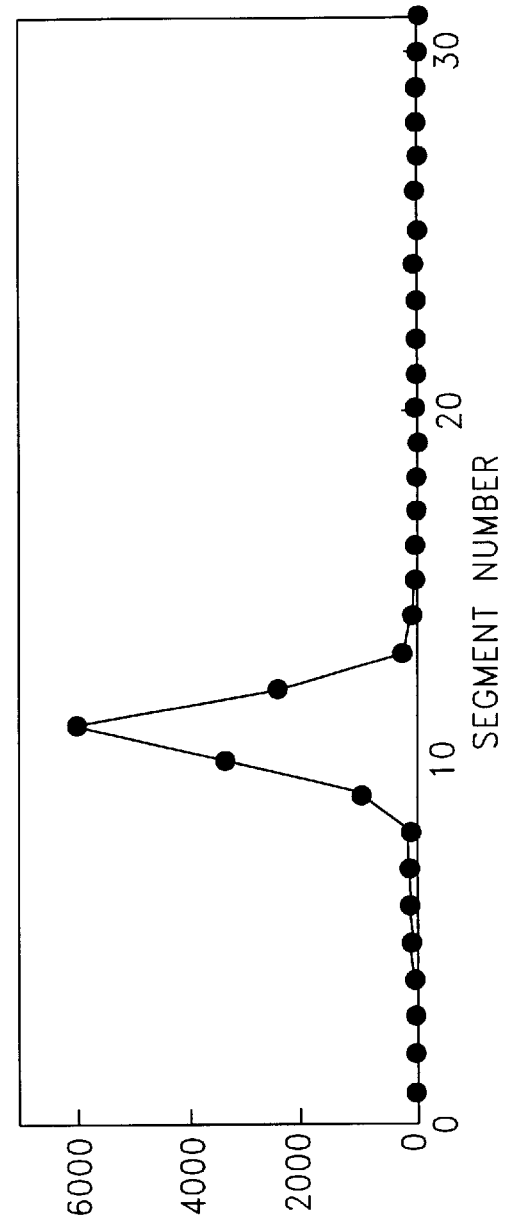
Figure 2C:
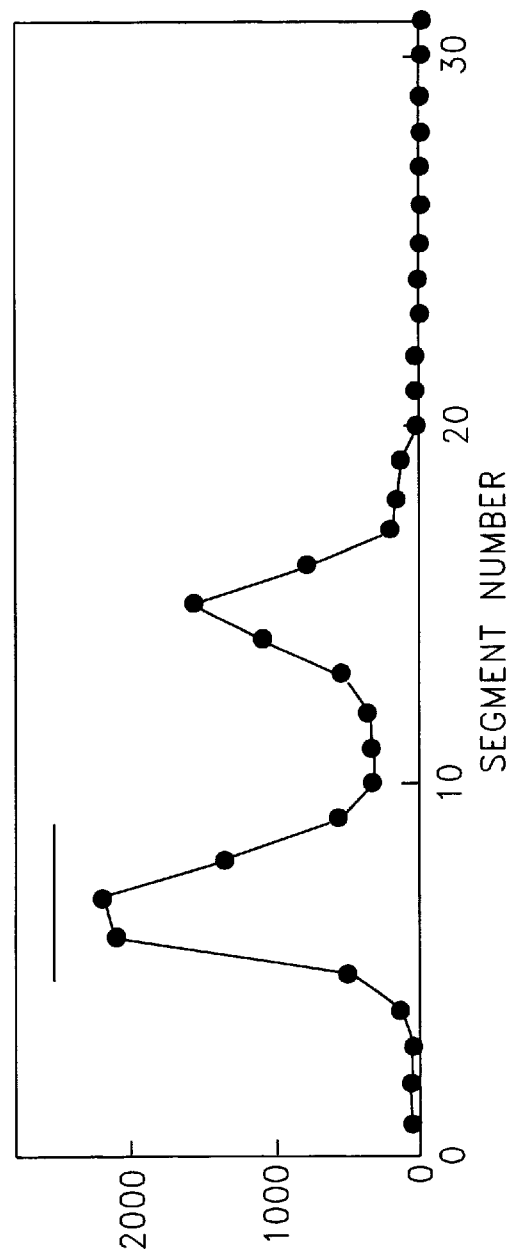
Figure 2D:
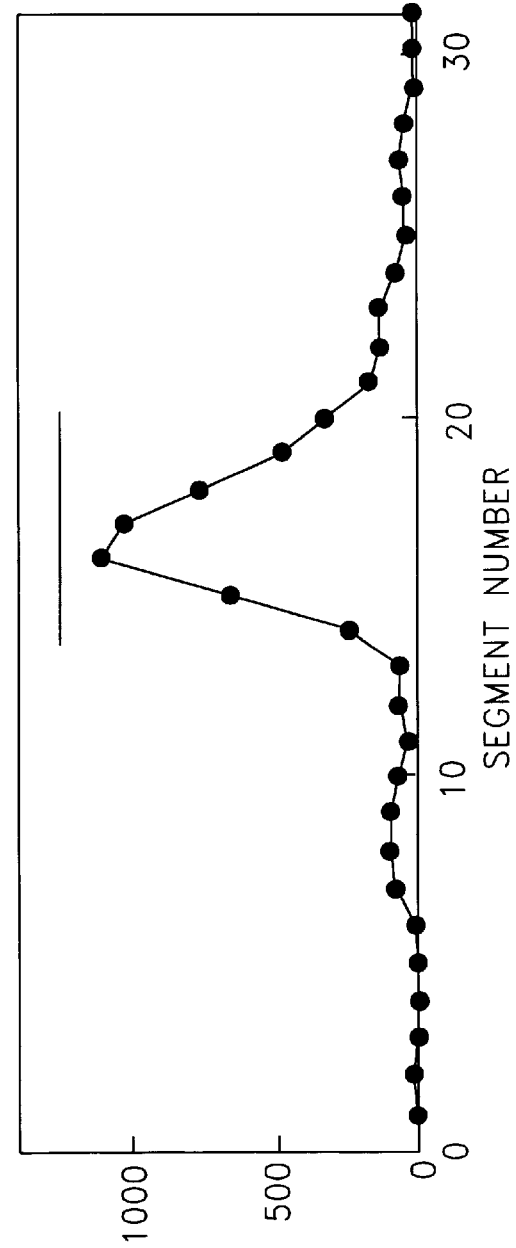

It is assumed that a fast moving peak in FIG. 2C (peak not indicated by the horizontal bar in FIG. 2C) corresponds to an unreacted substance brought about by incomplete N-deacetylation.

Figure 3:
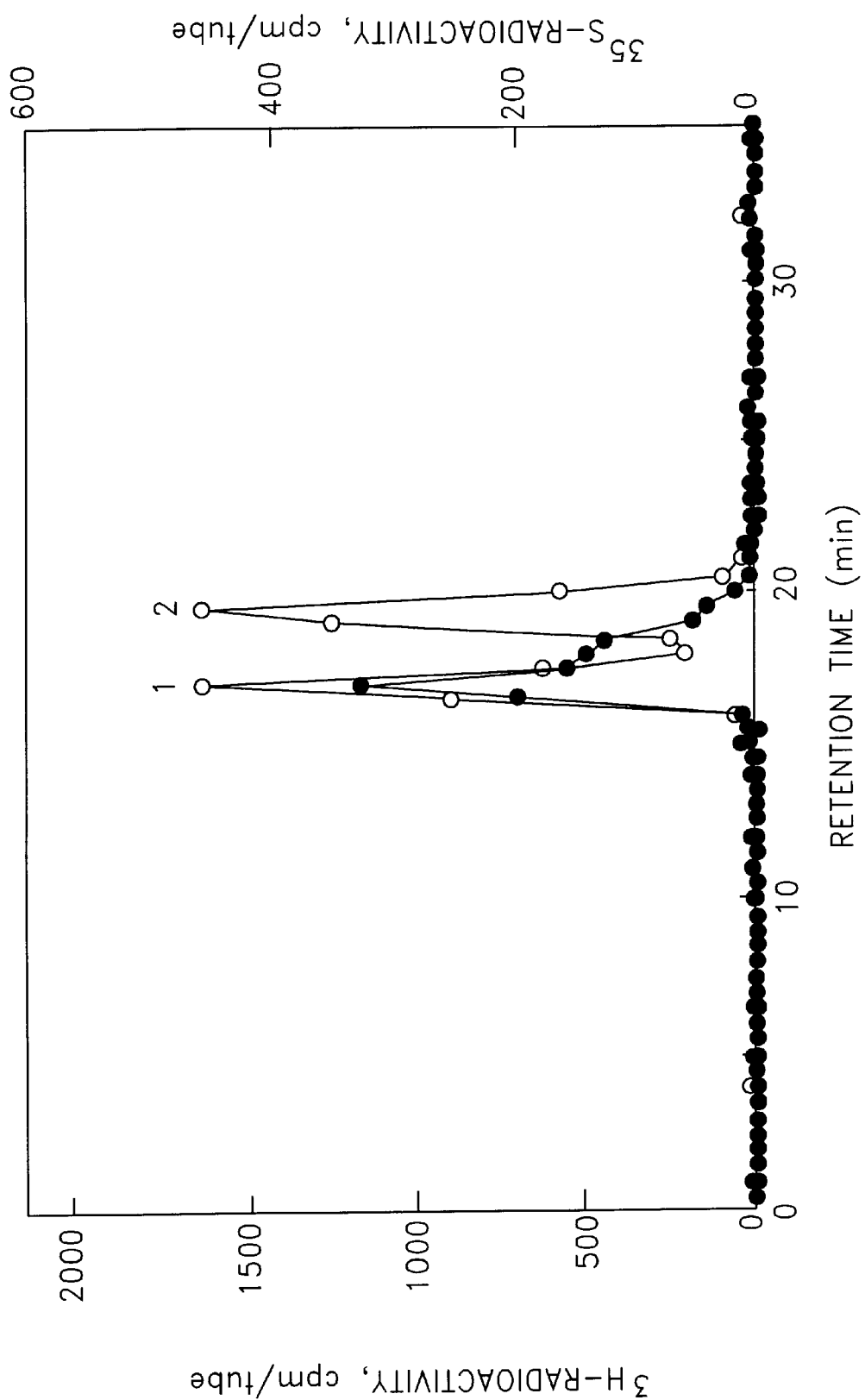
FIG. 3 shows separation by HPLC for substances obtained from SLN after deamination and reduction with NaBH$_4$.

A peak of a substance obtained after the deamination and the reduction with NaBH$_4$ (indicated by a horizontal bar shown in FIG. 2D) was mixed with the standard sulfated disaccharides to perform high-performance liquid chromatography (HPLC) by using a column of Whatman Partisil 10-SAX (4.5×25 cm) equilibrated with 5 mM KH$_2$PO$_4$. The column was developed with 5 mM KH$_2$PO$_4$. The flow rate was 1 ml/minute, and the temperature of the column was 40° C. Fractionation was performed with each fraction volume of 0.5 ml. Obtained fractions were mixed with 4 ml of Clearsol respectively to quantitatively measure the radioactivity. Results are shown in FIG. 3. In FIG. 3, open circles indicate the radioactivity of $^3$H, and closed circles indicate the radioactivity of $^{35}$S. Peaks 1 and 2 are [$^3$H]Gal(6S)β1—4AManR and [$^3$H]Galβ1—4AManR(6S) (standard sulfated disaccharides) respectively (Shaklee, P. N. and Conrad, H. E. (1986), *Biochem. J.*, 235, 225–236).

According to FIG. 3, it was demonstrated that major $^{35}$S-radioactivity was eluted together with [$^3$H]Gal(6S)β1× 4AManR, however, no $^{35}$S-radioactivity peak was detected at the position of [$^3$H]Galβ1—4AManR(6S). Therefore, it has been demonstrated that the sulfate group is transferred to hydroxyl group at C-6 position of the Gal residue by chondroitin 6-sulfotransferase, however, the sulfate group is not transferred to hydroxyl group at 0-6 position of the GlcNAc residue.

Example 3

Sensitivity of SL1L1 Including Transferred $^{35}$SO$_4$ and SL2L4 Including Transferred $^{35}$SO$_4$ to Digestion with β-Galactosidase In order to obtain information on the position of the sulfate group transferred to SL1L1 and SL2L4, the sensitivity to digestion with β-galactosidase was investigated for SL1L1 including transferred $^{35}$SO$_4$ and SL2L4 including transferred $^{35}$SO$_4$.

SL1L1 including transferred $^{35}$SO$_4$ or SL2L4 including transferred $^{35}$SO$_4$ was digested with neuraminidase in order to remove terminal sialic acid. Desialylated substances were separated by means of paper electrophoresis. After the electrophoresis, the desialylated products originating from SL1L1 including transferred $^{35}$SO$_4$ and SL2L4 including transferred $^{35}$SO$_4$ were eluted from the filter paper, lyophilized, mixed with non-radioactive L1L1 and non-radioactive L2L4, respectively, and digested with β-galactosidase.

The mixture of the desialylated product including transferred $^{35}$SO$_4$ and the non-radioactive oligosaccharide was subjected to gel filtration chromatography before or after the digestion with β-galactosidase. Eluted fractions from the gel filtration column were monitored on the basis of the absorbance at 210 nm and the radioactivity of $^{35}$S. FIG. 4 shows results for the mixture of the desialylated product of SL1L1 including transferred $^{35}$SO$_4$ and the non-radioactive L1L1 . FIG. 5 shows results for the mixture of the desialylated product of SL2L4 including transferred 35SO$_4$ and the non-radioactive L2L4. In FIGS. 4 and 5, A and C show the results obtained before the digestion with β-galactosidase, and B and D show the results obtained after the digestion with β-galactosidase. In FIGS. 4 and 5, C and D show the absorbance at 210 nm, and A and B show the radioactivity of 0.5 ml fractions.

With reference to the results obtained before the digestion with β-galactosidase, the desialylated products originating from SL1L1 and SL2L4 including transferred $^{35}$SO$_4$ were eluted at positions of sulfated L1L1 (FIG. 4A) and sulfated L2L4 (FIG. 5A) respectively. This fact demonstrated that the desialylation proceeded completely.

Figure 4A:
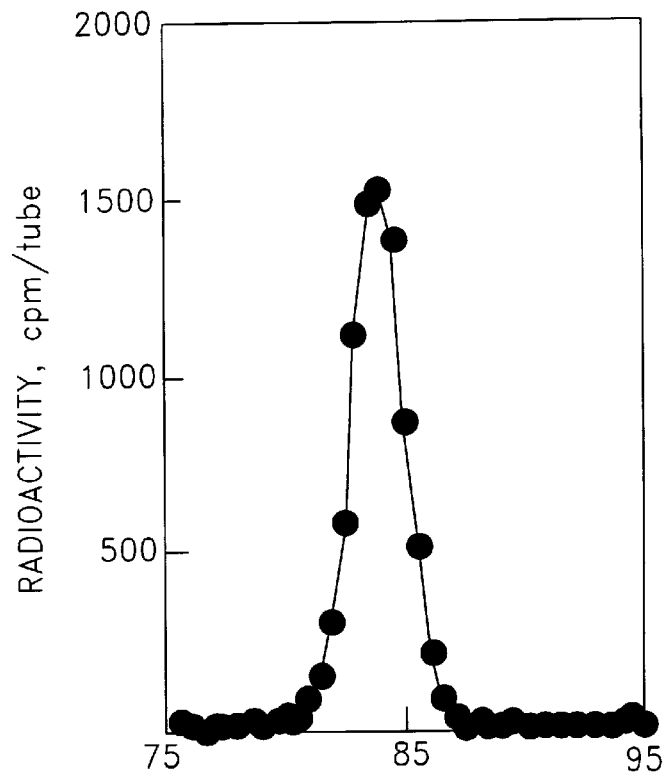
FIG. 4 shows results of gel filtration chromatography for desialylated products obtained from sulfated NeuAcα2—3Galβ1—4GlcNAcβ1—3Galβ1—4GlcNAc (SL1L1) before and after digestion with β-galactosidase.
Figure 4B:
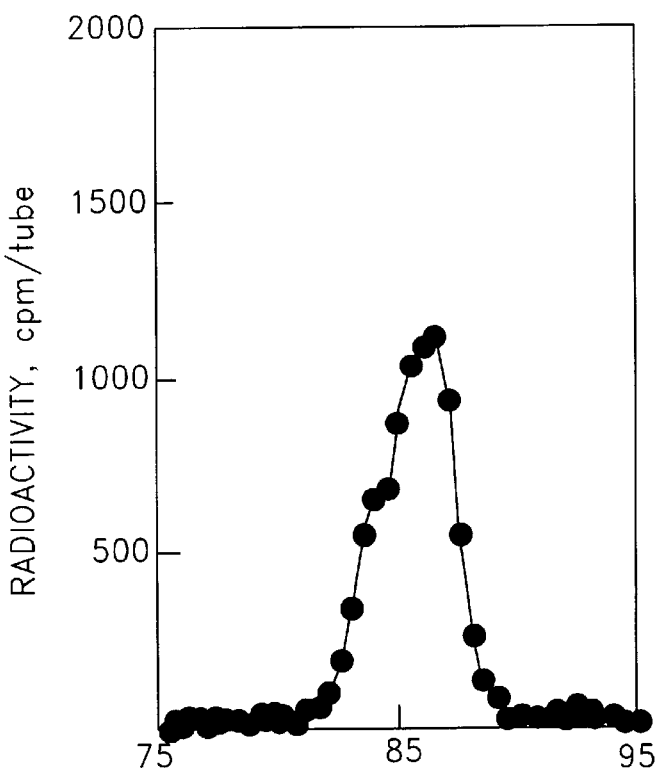
Figure 4C:
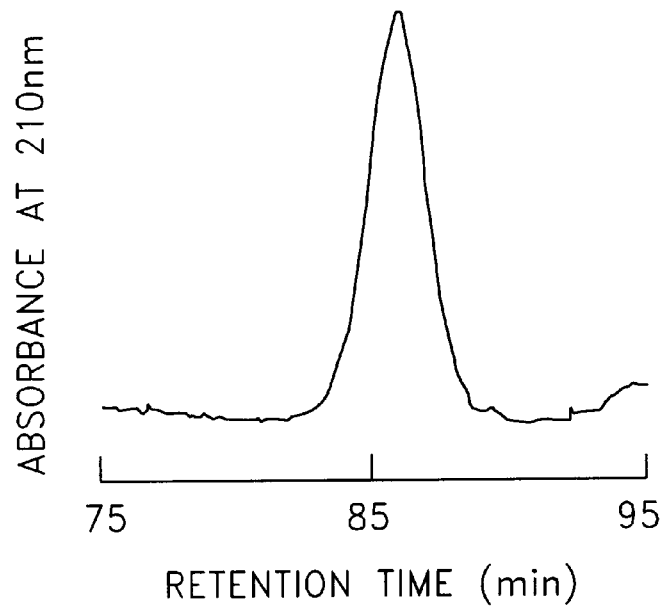
Figure 4D:
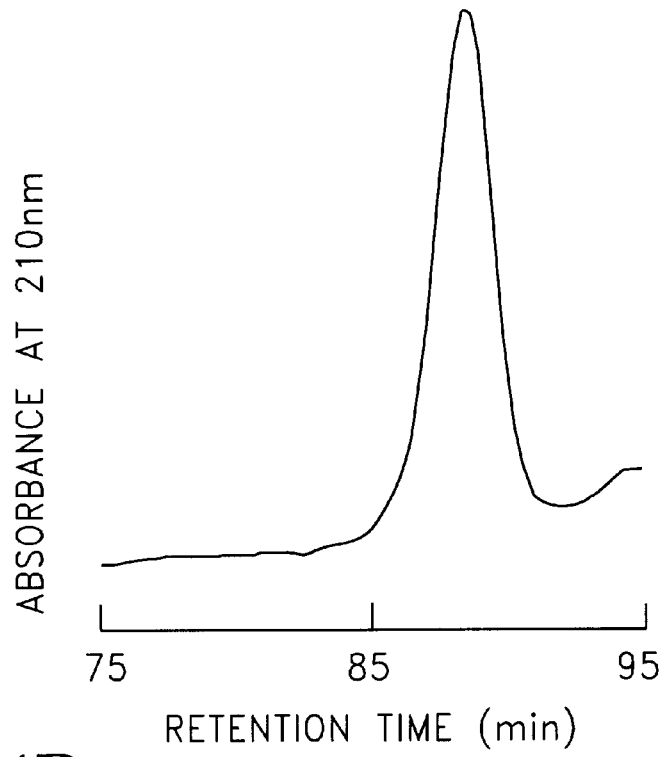

After the digestion with β-galactosidase of the mixture of the desialylated product of SL1L1 including transferred $^{35}SO_4$ and the non-radioactive L1L1, the absorbance at 210 nm originating from the non-radioactive L1L1 was completely migrated to a slower eluting position (FIG. 4D). On the other hand, about ⅓ of the $^{35}S$-radioactivity was still eluted at the position of sulfated L1L1 (FIG. 4B). These results suggested that about ⅓ of $^{35}SO_4$ transferred to SL1L1 was positioned at the Gal residue located on the non-reducing-end side.

Figure 5A:
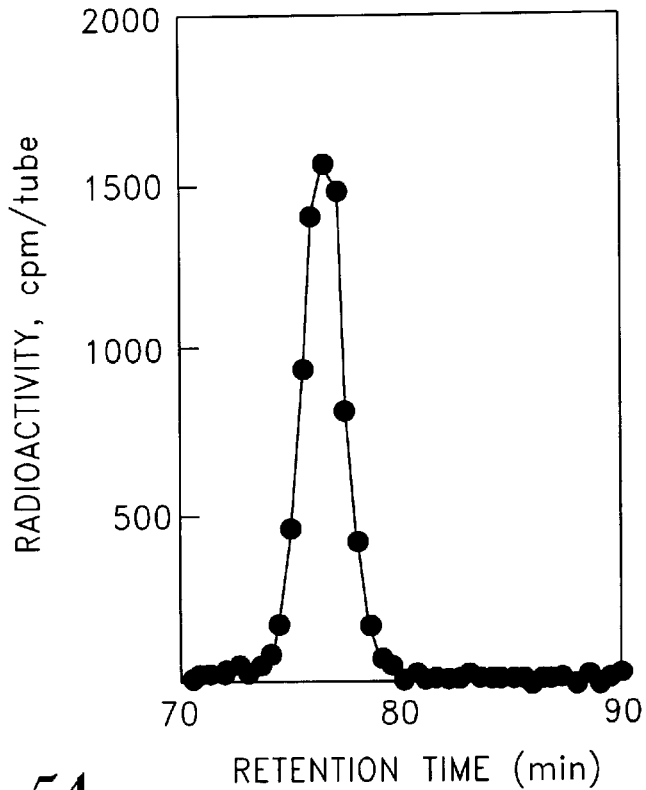
FIG. 5 shows results of gel filtration chromatography for desialylated products obtained from sulfated NeuAcα2—3Galβ1—4GlcNAc(6S)β1—3Gal(6S)β1—4GlcNAc(6S) (SL2L4) before and after digestion with β-galactosidase.
Figure 5B:
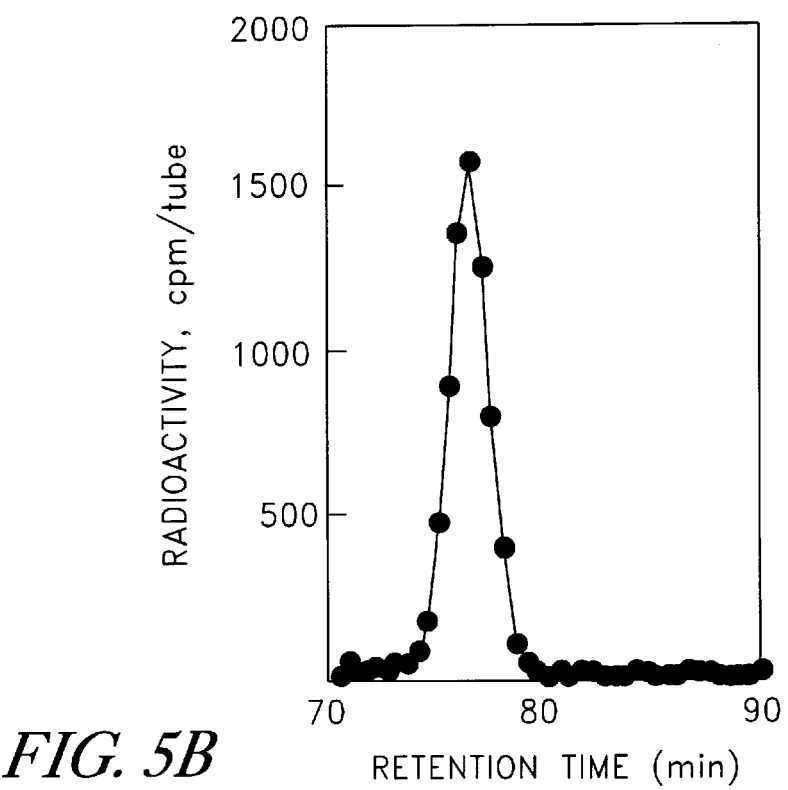
Figure 5C:
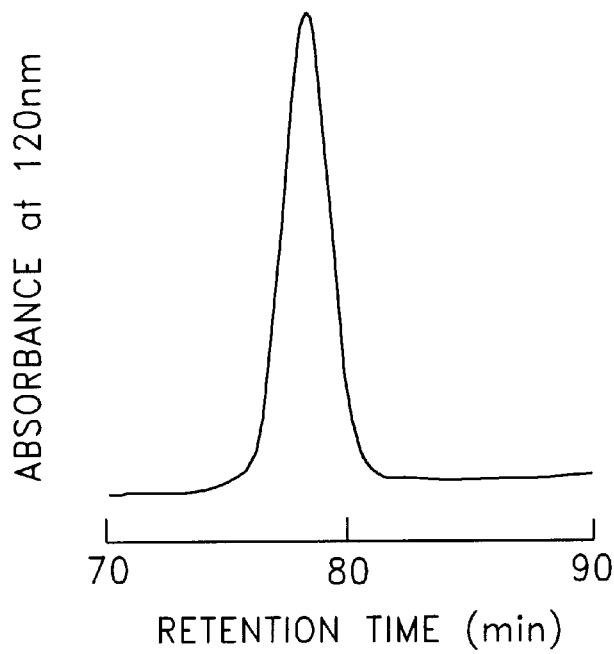
Figure 5D:
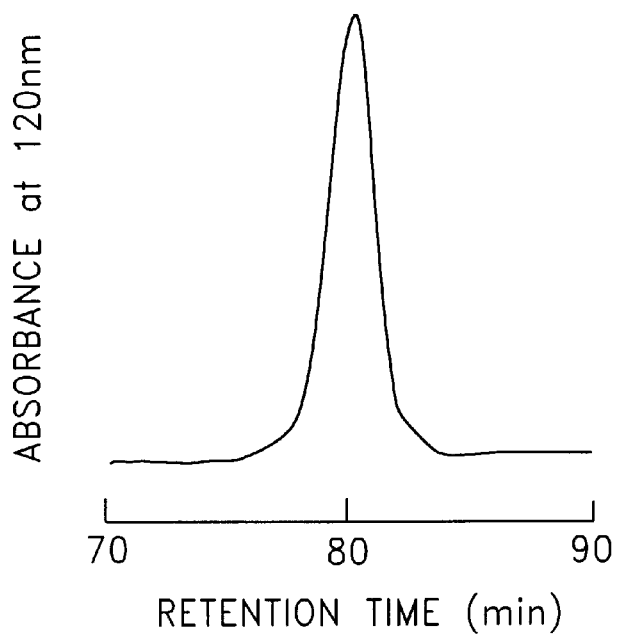

Sulfated L1L1 including transferred $^{35}SO_4$ was prepared and digested with β-galactosidase. As a result, no significant change occurred in the ratio of the substances including transferred $^{35}SO_4$ resistant to β-galactosidase (data are not shown herein). These results suggest that sialic acid located on the non-reducing end does not affect the distribution of transferred sulfate group. On the contrary, the desialylated product originating from SL2L4 including transferred $^{35}SO_4$ was generally insensitive to β-galactosidase (FIG. 5B), while non-radioactive L2L4 was completely degraded (FIG. 5D). According to these results, it has been demonstrated that all sulfate groups transferred to SL2L4 are located on the Gal residue located on the non-reducing end.

What is claimed is:

1. A method for producing a sulfated non-fucosylated lactosamine oligosaccharide, consisting essentially of the steps of:
   placing a sulfotransferase, a sulfate group donor, and a lactosamine oligosaccharide which is not fucosylated together in an aqueous solution, wherein said sulfotransferase is capable of transferring a sulfate group to a hydroxyl group at the C-6 position of a galactose residue in the lactosamine oligosaccharide and wherein said sulfotransferase transfers substantially no sulfate to a fucosylated lactosamine oligosaccharide, whereby said sulfotransferase transfers a sulfate group from said sulfate group donor to the hydroxyl group at position C-6 of the galactose residue present in the non-fucosylated lactosamine oligosaccharide to produce a sulfated lactosamine oligosaccharide which is not fucosylated; and
   recovering the sulfated non-fucosylated lactosamine oligosaccharide.

2. The method according to claim 1, wherein said sulfotransferase further has a property that a sulfate transferring activity to a lactosamine oligosaccharide in which an N-acetylglucosamine residue adjacent to the reducing-end side of a galactose residue is not sulfated at the C-6 position thereof is lower than that to a lactosamine oligosaccharide in which the N-acetylglucosamine residue adjacent to the reducing-end side of the galactose residue is sulfated at the C-6 position, and wherein said lactosamine oligosaccharide which is not fucosylated is sulfated at the C-6 position of a N-acetylglucosamine residue adjacent to the reducing-end side of the galactose residue.

3. The method according to claim 2, wherein said lactosamine oligosaccharide which is not fucosylated is selected from the group consisting of oligosaccharides having the following formulas:

Gal—GlcNAc (6S)—R

SA—Gal—GlcNAc (6S)—R wherein Gal is a galactose residue, GlcNAc is an N-acetylglucosamine residue, SA is a sialic acid residue, (6S) indicates that the hydroxyl group at the C-6 position is sulfated,—represents a glycoside linkage, and R is a hydrogen atom or a sugar chain containing 1 to 17 sugars.

4. The method according to claim 2, wherein said sulfotransferase is a sulfotransferase having the following physical and chemical properties:
   (1) action:
       the sulfotransferase transfers a sulfate group from a sulfate group donor to hydroxyl group at C-6 position of N-acetylgalactosamine residue or galactose residue of glycosaminoglycan;
   (2) substrate specificity:
       the sulfotransferase transfers the sulfate group to chondroitin, chondroitin sulfate A, chondroitin sulfate C, and keratan sulfate, but the sulfate group is not substantially transferred to chondroitin sulfate E, dermatan sulfate, and heparan sulfate;
   (3) optimum reaction pH:
       the sulfotransferase has an optimum reaction pH in the vicinity of 6.4;
   (4) activation:
       the activity of the sulfotransferase is increased by protamine or $MnCl_2$;
   (5) molecular weight:
       the sulfotransferase has a molecular weight of about 75 kilodaltons as estimated by sodium dodecyl sulfate-polyacrylamide gel electrophoresis under a reduced condition.

5. The method according to claim 4, wherein said lactosamine oligosaccharide which is not fucosylated is selected from the group consisting of oligosaccharides represented by the following formulas:

Gal—GlcNAc(6S)—R

SA—Gal—GlcNAc(6S)—R wherein Gal is a galactose residue, GlcNAc is an N-acetylglucosamine residue, SA is a sialic acid residue, (6S) indicates that the hydroxyl group at the C-6 position is sulfated,—represents a glycoside linkage, and R is a hydrogen atom or a sugar chain containing 1 to 17 sugars.

6. The method according to claim 5, wherein said sugar chain containing 1 to 17 sugars has a repeating structure composed of Gal—GlcNAc, wherein Gal is a galactose residue, GlcNAc is an N-acetylglucosamine residue, and— represents a glycoside linkage.

7. The method according to claim 5, wherein said lactosamine oligosaccharide is selected from the group consisting of oligosaccharides represented by the following formulas:

Gal—GlcNAc(6S)—Gal(6S)—GlcNAc(6S)

SA—Gal—GlcNAc(6S)—Gal(6S)—GlcNAc(6S)

wherein Gal is a galactose residue, GlcNAc is an N-acetylglucosamine residue, SA is a sialic acid residue, (6S) indicates that the hydroxyl group at the C-6 position is sulfated, and—represents a glycoside linkage.

8. The method according to claim 5, wherein said sulfated lactosamine oligosaccharide is selected from the group consisting of sulfated lactosamine oligosaccharides represented by the following formulas:

Gal(6S)—GlcNAc(6S)—R

SA—Gal(6S)—GlcNAc(6S)—R wherein Gal is a galactose residue, GlcNAc is an N-acetylglucosamine residue, SA is a sialic acid residue, (6S) indicates that the hydroxyl group at the C-6 position is sulfated,—represents a glycoside linkage, and R is a hydrogen atom or a sugar chain containing 1 to 17 sugars.

9. The method according to claim 5, wherein said sulfated lactosamine oligosaccharide is selected from the group consisting of sulfated lactosamine oligosaccharides represented by the following formulas:

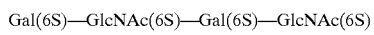

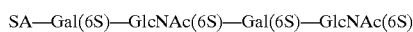

wherein Gal is a galactose residue, GlcNAc is an N-acetylglucosamine residue, SA is a sialic acid residue, (6S) indicates that the hydroxyl group at the C-6 position is sulfated, and—represents a glycoside linkage.

10. The method according to claim 5, wherein said sialic acid is N-acetylneuraminic acid.

11. The method according to claim 7, wherein said sialic acid is N-acetylneuraminic acid.

12. The method according to claim 8, wherein said sialic acid is N-acetylneuraminic acid.

13. The method according to claim 9, wherein said sialic acid is N-acetylneuraminic acid.

* * * * *